United States Patent
Sättler et al.

(10) Patent No.: US 6,877,363 B2
(45) Date of Patent: Apr. 12, 2005

(54) CHROMATOGRAPHY COLUMN

(75) Inventors: Günther Sättler, Reinheim (DE); Hans-Dieter Pohl, Pfungstadt (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 10/398,610

(22) PCT Filed: Aug. 30, 2001

(86) PCT No.: PCT/EP01/10010

§ 371 (c)(1), (2), (4) Date: Apr. 7, 2003

(87) PCT Pub. No.: WO02/31490

PCT Pub. Date: Apr. 18, 2002

(65) Prior Publication Data

US 2004/0020274 A1 Feb. 5, 2004

(51) Int. Cl.$^7$ ................................................. G01N 30/60
(52) U.S. Cl. ....................... 73/61.53; 96/104; 96/106; 210/198.2
(58) Field of Search ........................... 73/23.39, 61.53; 96/104, 106; 210/198.2

(56) References Cited

U.S. PATENT DOCUMENTS

| 4,670,141 A | | 6/1987 | Shackelford et al. ..... 210/198.2 |
| 4,737,284 A | * | 4/1988 | Hauke et al. ............ 210/198.2 |
| 4,806,238 A | * | 2/1989 | Sattler et al. ............ 210/198.2 |
| 5,227,059 A | | 7/1993 | Shepherd .................... 73/61.53 |
| 5,342,515 A | | 8/1994 | Radmacher .............. 210/198.2 |
| 5,651,886 A | | 7/1997 | Hoffmann et al. ........ 210/198.2 |

FOREIGN PATENT DOCUMENTS

| DE | 41 14 766 | 12/1992 | |
| EP | 0156520 | 10/1985 | ............. 210/198.2 |

* cited by examiner

Primary Examiner—Daniel S. Larkin
(74) Attorney, Agent, or Firm—Millen, White, Zelano & Branigan, P.C.

(57) ABSTRACT

The invention relates to a chromatography column for high-pressure liquid chromatography, which can be provided with different connection systems, such as a cartridge retaining device or a reducing screw. The column tube (1, 11) of the inventive chromatography column has an external thread (4,18) at each end and at least one groove (3,14).

4 Claims, 2 Drawing Sheets

CHROMATOGRAPHY COLUMN

The invention relates to a chromatography column for high-pressure liquid chromatography, which, owing to its design, can be provided with various connection systems, such as a cartridge holder or a thread adapter.

Two different systems are known for connection of HPLC columns: chromatography columns for direct connection to eluent feed and discharge or cartridge systems with replaceable column cartridges.

Chromatography columns usually have an external thread onto which the connections (adapters) for eluent feed and discharge can be screwed. In addition, sealing and filter elements are frequently incorporated into the thread adapter. By contrast, column cartridges do not have direct screw-joint means. They are clamped in cartridge holders or, as described in DE 35 19 725 or G 90 05 896, provided with a removable screw joint. The advantage of column cartridges is that on replacement of a spent column, it is only necessary to purchase a replacement column cartridge, but not the reversible connection or clamping system. After buying the entire cartridge system once, the consumer accordingly only requires the column cartridges. Without the connection or clamping system, however, column cartridges cannot be used. Consumers who do not have a connection or clamping system have to procure chromatography columns with an external thread and thread adapter.

In turn, suppliers of chromatography columns have to offer corresponding columns for each system. For a particular type of support material and column size, a supplier therefore has to offer at least two products: a column with direct thread adapter and a cartridge column. This is inconvenient in production and filling and requires twice the stocks.

The object of the present invention was therefore to provide a chromatography column which enables universal use in both connection systems.

It has been found that a universal chromatography column can be provided if a cartridge column having grooves for the attachment of the cartridge screw joint is additionally provided with an external thread.

The present invention therefore relates to a chromatography column consisting of a sorbent-filled column tube which has filter and sealing elements at both ends, characterised in that the column tube is provided at both ends with at least one groove and an external thread.

In a preferred embodiment, the chromatography column according to the invention has at both ends of the column tube an external thread and an annular groove incorporated into the external thread.

The present invention furthermore relates to a cartridge system with connections for solvent feed and discharge which contains a chromatography column according to the invention as a column cartridge.

The present invention moreover relates to the use of a chromatography column according to the invention for the chromatographic separation of at least two substances.

The figures show a preferred embodiment of the chromatography column according to the invention. Since the column preferably has a symmetrical construction, only one end of the column is shown in each case.

The chromatography column according to the invention corresponds to known chromatography columns in size, shape, material and filling. The column tube is typically filled with a sorbent and sealed with filter and sealing elements. Filter and sealing elements are known to the person skilled in the art. The column tube preferably consists of metal, for example stainless steel. At least one groove and an external thread are provided at both ends on the outside of the column tube. The external thread corresponds to that of a chromatography column for direct screw connection. In addition, at least one, preferably annular groove is incorporated into the column tube in the external thread or above or below the external thread. This groove enables integration of the chromatography column into a cartridge system. A pre-column is integrated, depending on the use of the chromatography column, as is known for columns with external thread or cartridge systems (for example EP 0 268 185).

In a preferred embodiment, the chromatography column corresponds to an RT ready-made stainless-steel column with external thread which can be purchased, for example, from Merck KGaA, Germany, into the ends of whose column tube a recess for the accommodation of filter and sealing element has additionally been incorporated internally and an annular groove has additionally been incorporated externally at the ends in such a way that the column can be employed in a cartridge system corresponding to EP 0 268 185, such as, for example, the manu-CART® cartridge system from Merck KGaA.

The chromatography column according to the invention can be employed in any cartridge system in which the connections for solvent feed and discharge are fixed via half-shells, which are inserted into the grooves at the ends of the column.

The chromatography column according to the invention achieves a simplification of the product range for customers and manufacturers. The chromatography column according to the invention combines all advantages of chromatography columns for direct connection with those of cartridge systems with replaceable column cartridges. The user can employ the chromatography column in both systems as desired. Mixed connection is also possible. The manufacturer can reduce the range of chromatography columns by half and thus saves logistics and storage costs.

Figure 1:
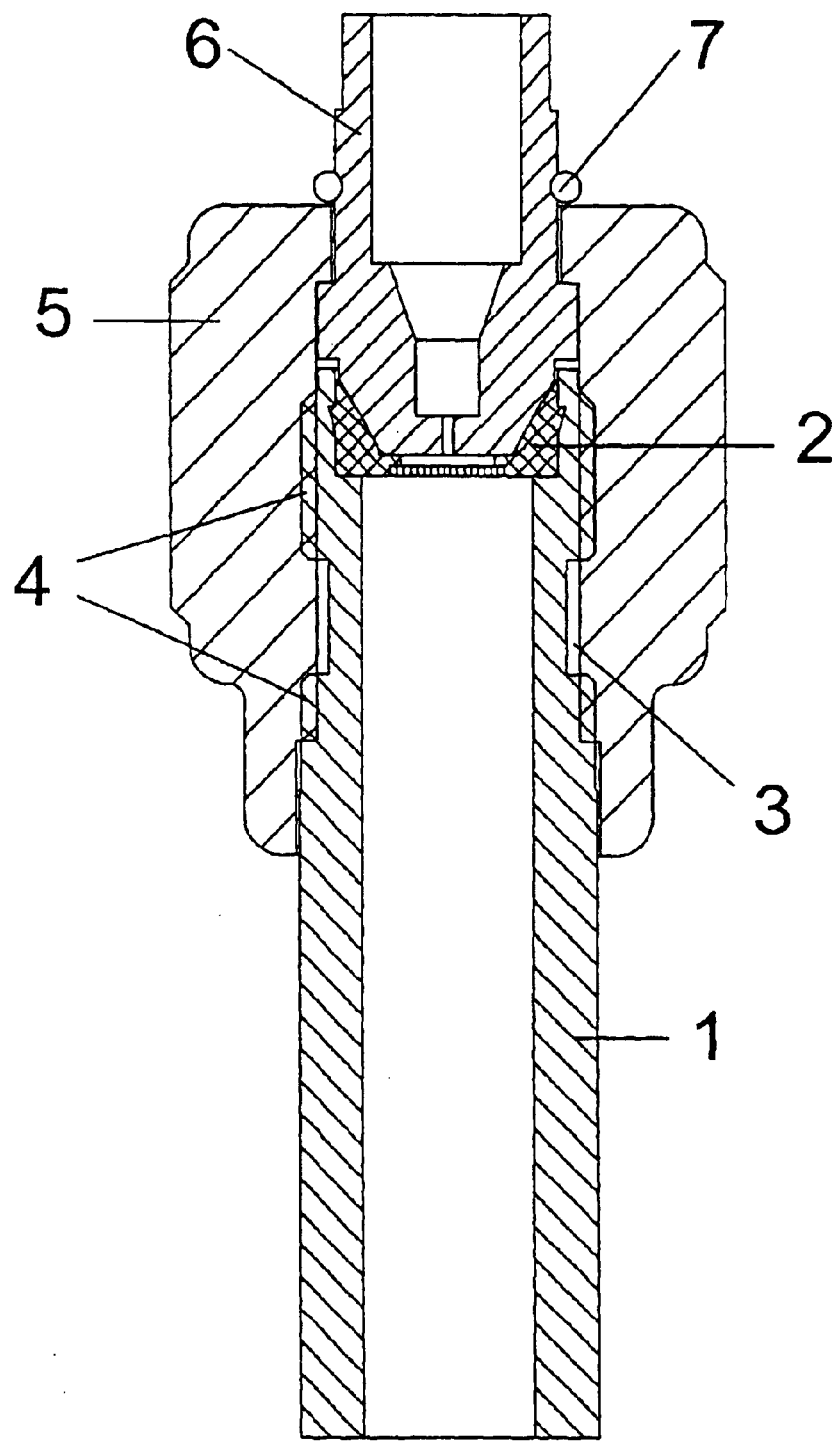
FIG. 1 shows a section through a column end with attached direct screw joint.

FIG. 1 shows a section through a column end with attached direct thread adapter. A sealing and filter element (2) has been introduced into the column tube (1) internally at the end of the tube. An annular groove (3) and an external thread (4) above and below the groove are located on the outside of the column tube (1). The groove (3) is not needed on use of a direct thread adapter. Instead, the union nut (5) is screwed onto the external thread (4). Through the union nut, the pressure piece (6) with securing ring (7) for connection of the eluent feed and discharge is fixed on the sealing and filter element (2).

Figure 2:
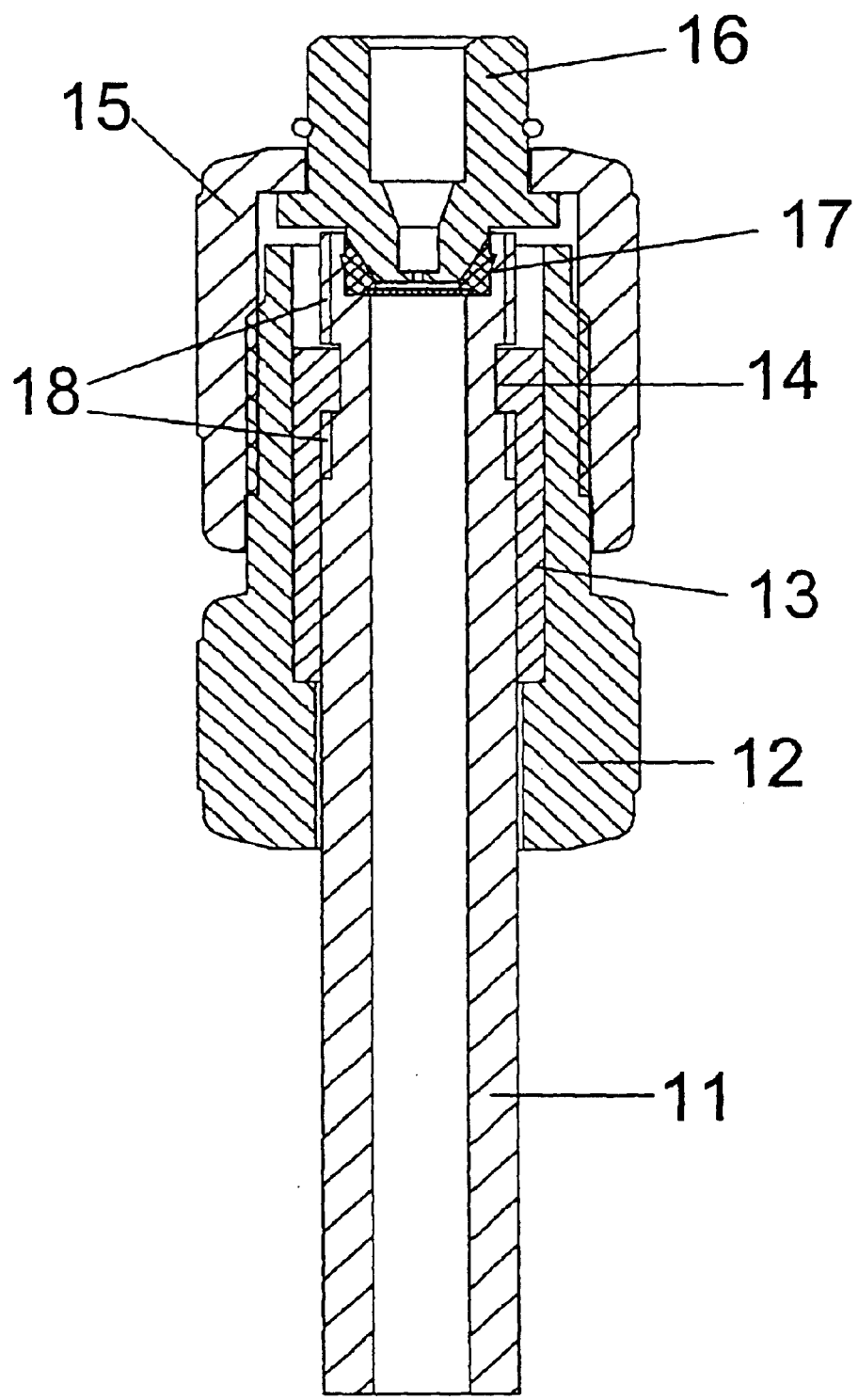
FIG. 2 shows a section through a column end with attached cartridge screw joint.

FIG. 2 shows a section through a column end with attached cartridge screw joint. A sealing and filter element (17) has been introduced into the column tube (11) internally at the ends. An annular groove (14) and an external thread (18) above and below the groove are located on the outside of the column tube (11). The external thread (18) is not needed on use of a cartridge screw joint. Instead, two half-shells (13), which hold the supporting nut (12) in position, are in this case placed against the groove (14). A union nut (15) is screwed onto the supporting nut (12) and again fixes the pressure piece (16) for connection of the eluent feed and discharge on the sealing and filter element (17).

Even without further details, it is assumed that a person skilled in the art will be able to utilise the above description in its broadest scope. The preferred embodiments and examples should therefore merely be regarded as descriptive disclosure which is absolutely not to be regarded as limiting in any way.

The complete disclosure content of all applications, patents and publications mentioned above and below, in particular the corresponding application DE 100 50 402, filed on Dec. 10, 2000, is incorporated into this application by way of reference.

What is claimed is:

1. Chromatography column comprising a sorbent-filled column tube which has filter and sealing elements at both ends, wherein the column tube is provided at both ends with an external thread, the external thread having at least one annular groove incorporated therein.

2. Cartridge system with connections for solvent feed and discharge, characterised in that it contains a chromatography column corresponding to claim 1 as a column cartridge.

3. Chromatograph column for chromatographic separation of at least two substances comprising a sorbent-filled column tube which has filter and sealing elements at both ends, wherein the column tube is provided at both ends with an external thread, the external thread having at least one annular groove incorporated therein intermediate the ends of the thread.

4. Cartridge system with connections for solvent feed and discharge, characterised in that it contains a chromatography column corresponding to claim 3 is a column cartridge.

* * * * *

UNITED STATES PATENT AND TRADEMARK OFFICE
CERTIFICATE OF CORRECTION

PATENT NO. : 6,877,363 B2
DATED : April 12, 2005
INVENTOR(S) : Guenther Saettler It is certified that error appears in the above-identified patent and that said Letters Patent is hereby corrected as shown below:

Title page,
Insert Item -- [30] Foreign Application Priority Data
October 12, 2000 (DE) 100 504 02.7 --

Column 4,
Line 4, reads "chromatograph" should read -- chromatography --
Line 13, reads "is" should read -- as --

Signed and Sealed this

Nineteenth Day of July, 2005

JON W. DUDAS
*Director of the United States Patent and Trademark Office*